US00PP27270P2

(12) United States Plant Patent
Nishikawa

(10) Patent No.: US PP27,270 P2
(45) Date of Patent: Oct. 11, 2016

(54) ***BIDENS* PLANT NAMED 'HAFLPARE'**

(50) Latin Name: *Bidens triplinervia*
Varietal Denomination: Haflpare

(71) Applicant: Koichiro Nishikawa, Okayama (JP)

(72) Inventor: Koichiro Nishikawa, Okayama (JP)

( * ) Notice: Subject to any disclaimer, the term of this patent is extended or adjusted under 35 U.S.C. 154(b) by 33 days.

(21) Appl. No.: 14/544,724

(22) Filed: Feb. 9, 2015

(51) Int. Cl.
*A01H 5/02* (2006.01)

(52) U.S. Cl.
USPC ..... Plt./410

(58) Field of Classification Search
USPC ..... Plt./263.1, 410
See application file for complete search history.

*Primary Examiner* — Susan McCormick Ewoldt
*Assistant Examiner* — Karen Redden
(74) *Attorney, Agent, or Firm* — C. A. Whealy

(57) ABSTRACT

A new and distinct cultivar of *Bidens* plant named 'Haflpare', characterized by its upright, outwardly spreading to somewhat trailing and mounding plant habit; vigorous growth habit; freely branching habit; freely flowering habit; long flowering period; inflorescences with deep orange and yellow bi-colored ray florets and bright yellow-colored disc florets; and strong peduncles that hold the inflorescences above and beyond the foliar plane.

1 Drawing Sheet

Botanical designation: *Bidens triplinervia.*
Cultivar denomination: 'HAFLPARE'.

CROSS-REFERENCED TO RELATED APPLICATIONS

Title: *Bidens* Plant Named 'Haflrest'
Applicant: Koichiro Nishikawa
Filed: Concurrently with this application Ser. No. 14/544,725

Title: *Bidens* Plant Named 'Hafltibr'
Applicant: Koichiro Nishikawa
Filed: Concurrently with this application Ser. No. 14/544,732

Title: *Bidens* Plant Named 'Hafltifrpu'
Applicant: Koichiro Nishikawa
Filed: Concurrently with this application Ser. No. 14/544,730

Title: *Bidens* Plant Named 'Hafltufr'
Applicant: Koichiro Nishikawa
Filed: Concurrently with this application Ser. No. 14/544,729.

BACKGROUND OF THE INVENTION

The present invention relates to a new and distinct cultivar of *Bidens* plant, botanically known as *Bidens triplinervia* and hereinafter referred to by the name 'Haflpare'.

The new *Bidens* plant is a product of a planned breeding program conducted by the Inventor in Okayama-ken, Japan. The objective of the breeding program is to create new freely-branching *Bidens* plants with unique ray floret coloration.

The new *Bidens* plant originated from a self-pollination made by the Inventor in Okayama-ken, Japan in January, 2010 of *Bidens triplinervia* 'K-SAIKA001', not patented. The new *Bidens* plant was discovered and selected by the Inventor as a single flowering plant from within the progeny of the stated self-pollination in a controlled greenhouse environment in Okayama-ken, Japan in May, 2010.

Asexual reproduction of the new *Bidens* plant by vegetative cuttings in a controlled environment in Okayama-ken, Japan since June, 2010 has shown that the unique features of this new *Bidens* plant are stable and reproduced true to type in successive generations.

SUMMARY OF THE INVENTION

Plants of the new *Bidens* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Haflpare'. These characteristics in combination distinguish 'Haflpare' as a new and distinct *Bidens* plant:

1. Upright, outwardly spreading to somewhat trailing and mounding plant habit.
2. Vigorous growth habit.
3. Freely branching habit.
4. Freely flowering habit.
5. Long flowering period.
6. Inflorescences with deep orange and yellow bi-colored ray florets and bright yellow-colored disc florets.
7. Strong peduncles that hold the inflorescences above and beyond the foliar plane.

Plants of the new *Bidens* differ primarily from plants of the parent, 'K-SAIKA001' in ray floret color as inflorescences of 'K-SAIKA001' have yellow and subdued orange bi-colored ray florets.

Plants of the new *Bidens* can be compared to plants of *Bidens triplinervia* 'Haflrest', disclosed in a U.S. Plant Patent application filed concurrently. In side-by-side comparisons conducted in Okayama-ken, Japan, plants of the new *Bidens* differed from plants of 'Hafltibr' in ray floret color as plants of 'Haflrest' have dark orange-colored ray florets with yellow-colored borders.

Plants of the new *Bidens* can be compared to plants of *Bidens triplinervia* 'Hafltibr', disclosed in a U.S. Plant Patent application filed concurrently. In side-by-side comparisons conducted in Okayama-ken, Japan, plants of the new *Bidens* differed from plants of 'Hafltibr' in plant size and ray floret color as plants of 'Hafltibr' are more compact than plants of the new *Bidens* and have orange-colored ray florets with orange red-colored central and lateral stripes.

Plants of the new *Bidens* can be compared to plants of *Bidens triplinervia* 'Hafltifrpu', disclosed in a U.S. Plant Patent application filed concurrently. In side-by-side comparisons conducted in Okayama-ken, Japan, plants of the new *Bidens* differed from plants of 'Hafltifrpu' in plant size and ray floret color as plants of 'Hafltifrpu' are more compact than plants of the new *Bidens* and have orange and yellow bi-colored ray florets.

Plants of the new *Bidens* can be compared to plants of *Bidens triplinervia* 'Hafltufr', disclosed in a U.S. Plant Patent application filed concurrently. In side-by-side comparisons conducted in Okayama-ken, Japan, plants of the new *Bidens* differed from plants of 'Hafltufr' in ray floret color as plants of 'Hafltufr' have ray florets with dark orange-colored centers and yellow to light yellow-colored apices.

Plants of the new *Bidens* can also be compared to plants of *Bidens triplinervia* 'Florbikanre', disclosed in U.S. Plant Pat. No. 24,867. In side-by-side comparisons conducted in Okayama-ken, Japan, plants of the new *Bidens* differed from plants of 'Florbikanre' in the following characteristics:

1. Plants of the new *Bidens* were taller than plants of 'Florbikanre'.
2. Plants of the new *Bidens* had longer and thicker lateral branches than plants of 'Florbikanre'.
3. Plants of the new *Bidens* had shorter leaves than plants of 'Florbikanre'.
4. Plants of the new *Bidens* and 'Florbikanre' differed in ray floret color as plants of 'Florbikanre' had light red-colored ray florets.
5. Plants of the new *Bidens* had shorter peduncles than plants of 'Florbikanre'.

BRIEF DESCRIPTION OF THE PHOTOGRAPH

The accompanying photograph illustrates the overall appearance of the new *Bidens* plant showing the colors as true as it is reasonably possible to obtain in colored reproductions of this type. Colors in the photograph may differ slightly from the color values cited in the detailed botanical description which accurately describe the colors of the new *Bidens* plant.

The photograph comprises a side perspective view of a typical flowering plant of 'Haflpare' grown in a container.

DETAILED BOTANICAL DESCRIPTION

The aforementioned photograph and following observations and measurements describe plants grown in 15-cm containers during December in a polyethylene-covered greenhouse in Cartago, Costa Rica and under cultural practices which approximate those generally used in commercial *Bidens* production. During the production of the plants, day temperatures averaged 26° C., night temperatures averaged 18° C. and light levels ranged from 12 to 15 moles per day. Plants were pinched two times and were 21 weeks old when the photograph and description were taken. In the following description, color references are made to The Royal Horticultural Society Colour Chart, 2007 Edition, except where general terms of ordinary dictionary significance are used.

Botanical classification: *Bidens triplinervia* 'Haflpare'.

Parentage: Self-pollination of *Bidens triplinervia* 'K-SAIKA001', not patented.

Propagation:

*Type*.—By vegetative tip cuttings.

*Time to initiate roots, summer*.—About one week at temperatures about 23° C.

*Time to initiate roots, winter*.—About two weeks at temperatures about 23° C.

*Time to produce a rooted young plant, summer*.—About three to four weeks at temperatures about 23° C.

*Time to produce a rooted young plant, winter*.—About four to five weeks at temperatures about 10° C. to 15° C.

*Root description*.—Fine, fibrous; white, close to 155D, in color.

*Rooting habit*.—Freely branching; dense.

Plant description:

*Plant and growth habit*.—Upright, outwardly spreading to somewhat trailing and mounding plant habit; vigorous growth habit and rapid growth rate.

*Branching habit*.—Freely branching habit with about 40 lateral branches developing per plant; dense and bushy appearance.

*Plant height*.—About 60 cm.

*Plant diameter or spread*.—About 90 cm.

*Lateral branches*.—Length: About 45 cm. Diameter: About 2 mm. Internode length: About 9 cm. Strength: Strong, flexible. Texture: Smooth, glabrous. Color: Close to 144B.

Leaf description:

*Arrangement*.—Opposite, simple.

*Length*.—About 3 cm.

*Width*.—About 2 cm.

*Shape*.—Roughly deltoid; pinnatisect.

*Apex*.—Acute.

*Base*.—Acute.

*Margin*.—Deeply incised; laciniate.

*Texture, upper and lower surfaces*.—Smooth, glabrous.

*Venation pattern*.—Pinnate.

*Color*.—Developing leaves, upper surface: Close to 137B. Developing leaves, lower surface: Close to 138B. Fully expanded leaves, upper surface: Close to N137A; venation, close to 137B. Fully expanded leaves, lower surface: Close to 137C; venation, close to 137A.

*Petioles*.—Length: About 1.7 cm. Diameter: About 0.7 mm. Texture, upper and lower surfaces: Smooth, glabrous. Color, upper surface: Close to N77A. Color, lower surface: Close to 146A.

Inflorescence description:

*Appearance*.—Single (daisy) inflorescence form with ray and disc florets; inflorescences positioned above and beyond the foliar plane on strong peduncles; inflorescences face mostly upright to outwardly.

*Flowering habit*.—Freely flowering habit with numerous inflorescences developing per plant.

*Fragrance*.—Sweet, honey-like.

*Natural flowering season*.—Long flowering period, plants flower continuously from spring until the autumn in temperate regions.

*Inflorescence longevity*.—Inflorescences last about one week on the plant; inflorescences not persistent.

*Inflorescence buds*.—Height: About 3 mm. Diameter: About 4 mm. Shape: Cylindrical. Color: Close to 151A.

*Inflorescence size*.—Total diameter: About 3.5 cm. Disc diameter: About 4 mm. Receptacle diameter: About 4 mm. Receptacle height: About 3 mm. Receptacle color: Close to 137B.

*Ray florets*.—Number of ray florets per inflorescence: Five arranged in a single whorl. Length: About 1.5 cm. Width: About 1 cm. Shape: Ovate to lanceolate. Apex: Rounded. Base: Obtuse. Margin: Entire. Texture, upper and lower surfaces: Smooth, glabrous. Color: When opening, upper surface: Close to N25C; towards the distal margins and apex, close to 8A. When opening, lower surface: Close to 169A; towards the distal margins and apex, close to 5C. Fully opened, upper surface: Close to N25C; towards the distal margins and apex, close to 8A; color does not fade with development. Fully opened, lower surface: Close to 169B; towards the distal margins and apex, close to 17B; color does not fade with development.

*Disc florets*.—Number of disc florets per inflorescence: About 42 massed at the center of the receptacle. Length: About 5 mm. Diameter: About 0.8 mm. Shape: Tubular; apex dentate. Color, when opening: Towards the apex, close to 12B; center and towards the base, close to 8D. Color, fully opened: Close to 17B.

*Phyllaries*.—Quantity per inflorescence: About eleven in two whorls. Length: About 3 mm. Width: About 1 mm. Shape: Lanceolate to filiform. Apex: Acute. Base: Truncate. Margin: Entire. Texture, upper and lower surfaces: Smooth, glabrous. Color, upper and lower surfaces: Close to 137B.

*Peduncles*.—Length, terminal peduncle: About 7.5 cm. Diameter: About 1 mm. Strength: Strong; flexible. Aspect: Erect to about 45° from vertical; peduncles holding inflorescences above and beyond the foliar plane. Texture: Smooth, glabrous. Color: Close to 144B.

*Reproductive organs*.—Androecium: Present on disc florets only. Quantity per disc floret: One. Filament length: About 0.5 mm. Filament color: Close to 145D. Anther shape: Lanceolate. Anther length: About 1 mm. Anther color: Close to 17B. Pollen amount: Moderate. Pollen color: Close to 21A. Gynoecium: Present on ray and disc florets. Pistil length: Less than 1 mm. Style length: Less than 1 mm. Style color: Close to 153D. Stigma shape: Bi-lobed. Stigma color: Close to 15A. Ovary color: Close to 145D.

*Seeds*.—Length: About 5 mm. Diameter: About 1 mm. Color: Close to 202A.

Disease & pest resistance: Plants of the new *Bidens* have not been shown to be resistant to pathogens and pests common to *Bidens* plants.

Garden performance: Plants of the new *Bidens* have exhibited good tolerance to rain and wind and have been observed to tolerate temperatures from about 1° C. to about 47° C.

It is claimed:

1. A new and distinct *Bidens* plant named 'Haflpare' as illustrated and described.

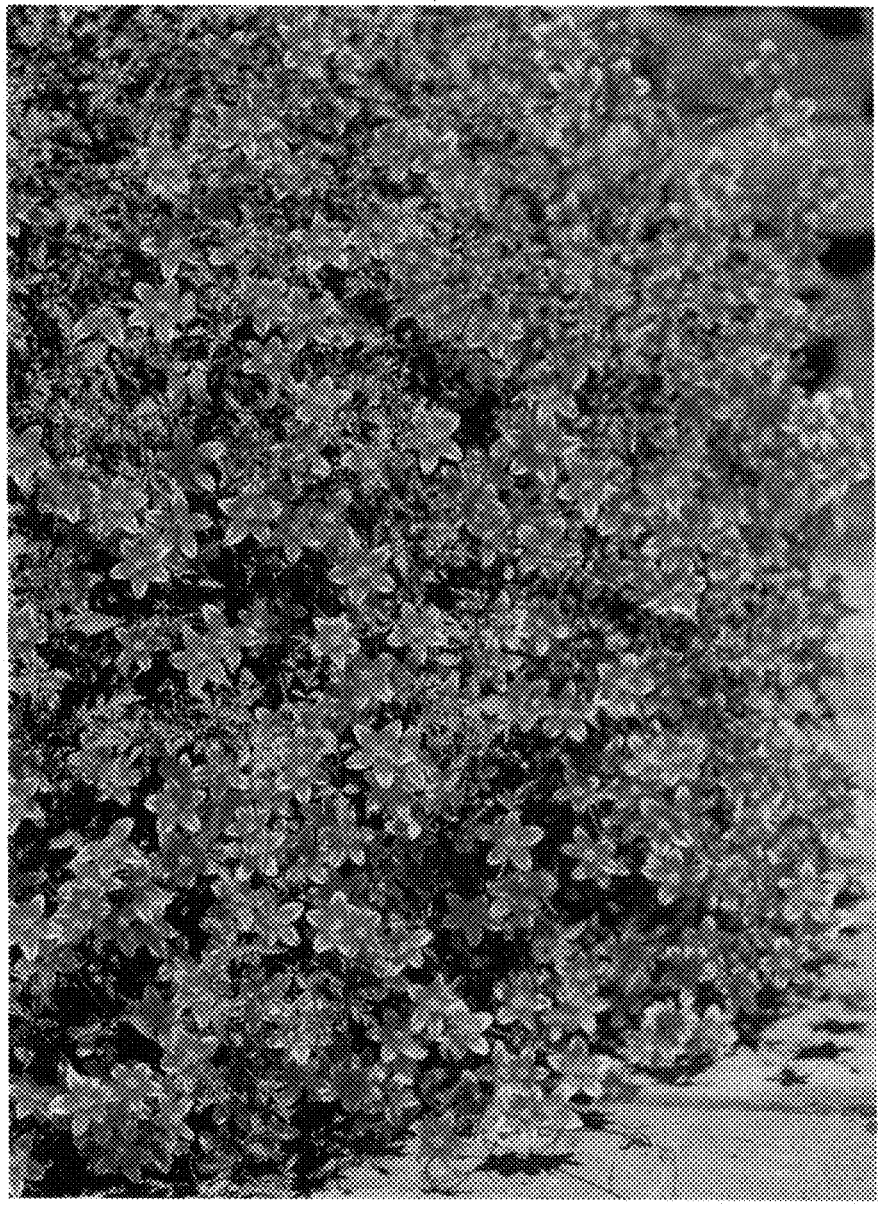

* * * * *